(12) United States Patent
Kolahi et al.

(10) Patent No.: US 8,915,147 B2
(45) Date of Patent: Dec. 23, 2014

(54) METHOD FOR OPERATING A RESONANCE MEASURING SYSTEM

(75) Inventors: Kourosh Kolahi, Duisburg (DE); Ralf Storm, Essen (DE)

(73) Assignee: KROHNE Messtechnik GmbH, Duisburg (DE)

( * ) Notice: Subject to any disclaimer, the term of this patent is extended or adjusted under 35 U.S.C. 154(b) by 118 days.

(21) Appl. No.: 13/701,945

(22) PCT Filed: Nov. 18, 2011

(86) PCT No.: PCT/EP2011/005815
§ 371 (c)(1),
(2), (4) Date: Feb. 19, 2013

(87) PCT Pub. No.: WO2012/113421
PCT Pub. Date: Aug. 30, 2012

(65) Prior Publication Data
US 2013/0199306 A1  Aug. 8, 2013

(30) Foreign Application Priority Data

Nov. 19, 2010  (DE) .......................... 10 2010 051 738
Feb. 25, 2011  (DE) .......................... 10 2011 012 498

(51) Int. Cl.
*G01F 1/84* (2006.01)
*G01F 1/74* (2006.01)
*G01N 9/00* (2006.01)

(52) U.S. Cl.
CPC ............ *G01F 1/8413* (2013.01); *G01F 1/8468* (2013.01); *G01F 1/74* (2013.01); *G01F 1/849* (2013.01); *G01N 9/002* (2013.01); *G01F 1/8422* (2013.01); *G01F 1/8436* (2013.01)
USPC .................................................... 73/861.355

(58) Field of Classification Search
USPC ...................... 73/861.355–861.357
See application file for complete search history.

(56) References Cited

U.S. PATENT DOCUMENTS

| | | | | |
|---|---|---|---|---|
| 5,381,697 A | * | 1/1995 | van der Pol | 73/861.356 |
| 5,473,949 A | * | 12/1995 | Cage et al. | 73/861.356 |
| 7,640,813 B2 | * | 1/2010 | Storm | 73/861.356 |
| 8,322,230 B2 | | 12/2012 | Weinstein | |
| 8,327,717 B2 | | 12/2012 | Weinstein | |
| 8,327,718 B2 | | 12/2012 | Weinstein | |
| 8,596,144 B2 | * | 12/2013 | Rieder | 73/861.55 |

FOREIGN PATENT DOCUMENTS

| | | |
|---|---|---|
| CA | 2 634 959 A1 | 7/2007 |
| EP | 1 845 346 A2 | 10/2007 |
| WO | 2008/152060 A1 | 12/2008 |
| WO | 2010/085980 A1 | 8/2010 |

* cited by examiner

*Primary Examiner* — Jewel V Thompson
(74) *Attorney, Agent, or Firm* — Roberts Mlotkowski Safran & Cole, P.C.; David S. Safran

(57) ABSTRACT

A method for operating a Coriolis mass flowmeter in which a simple and reliable detection of a multi-phase flow is implemented by determining at least one first measured value for at least one state variable that is dependent on the amplitude in a multi-phase medium, exciting the measuring tube with the oscillation generator to oscillate at a predetermined oscillation frequency and a first amplitude, and to oscillate with the excitation frequency and a second amplitude, detecting the resulting oscillation of the measuring tube and determining at least a second measured value for the state variable that is dependent on the amplitude in a multi-phase medium from the determined resulting oscillation, and using the deviation of at least one of the first measured value from at least a corresponding second value as an indicator for the presence of a multi-phase flow.

12 Claims, 3 Drawing Sheets

METHOD FOR OPERATING A RESONANCE MEASURING SYSTEM

BACKGROUND OF THE INVENTION

1. Field of the Invention

The invention relates to a method for operating a resonance measuring system, in particular in the form of a Coriolis mass flowmeter or in the form of a density measuring device, wherein the resonance measuring system has at least one measuring tube with a flowing medium, at least one oscillation generator, at least one oscillation sensor and at least one control and evaluation unit, wherein the measuring tube is excited by the oscillation generator to an oscillation with a predetermined excitation frequency and a first amplitude and the resulting oscillation of the measuring tube is detected by at least one oscillation sensor. Furthermore, the invention relates to a resonance measuring system, in particular in the form of a Coriolis mass flowmeter or in the form of a density measuring device that is operated with the above-mentioned method.

2. Description of Related Art

Resonance measuring systems have been known for a long time, not only in the form of Coriolis mass flowmeters, but also as density measuring devices, inter alia. These resonance measuring systems are in contact with a process wherein the process and the resonance measuring system mutually influence one another. Systems in which information about determining process variables (measurement variables) are encoded and/or systems in which working points are placed on the eigenfrequencies of the measuring system are generally the systems called resonance measuring systems, here. The following designs can be used on all of the systems fitting this definition, insofar as they have a measuring tube with medium flowing through it or able to be flowing through it. In the following, resonance measuring systems are shown using Coriolis mass flowmeters as an example, which is not to be seen as being limiting.

Coriolis mass flowmeters are used especially in industrial process measurement, where mass flow has to be determined with high accuracy. The functionality of Coriolis mass flowmeters is based on at least one measuring tube—oscillation element—with medium flowing through it being excited to oscillation with an oscillation generator, wherein the Coriolis inertial force caused by the medium having mass reacts on the walls of the measuring tube due to two orthogonal velocities—the flow and the measuring tube—. This reaction of the medium on the measuring tube leads to a change of the measuring tube oscillation compared to the oscillation state of the measuring tube when there is no flow. By detecting these particularities of the oscillation of the measuring tube with flow—phase differences between measuring tube sections that oscillate in phase when there is no flow in the measuring tube—, the mass flow through the measuring tube can be determined with a high accuracy. Accuracies of about 0.04% of the measured value can be achieved in homogeneous media with high-quality Coriolis mass flowmeters, which is why Coriolis mass flowmeters are often used in custody transfer.

If it is said that the measuring tube is excited with a predetermined excitation frequency and first amplitude, then the predetermined excitation frequency is usually meant as the eigenfrequency of a predetermined or desired eigenform, in which the measuring tube is to oscillate. The excitation frequency is then always corrected by a control and quasi given, should the eigenfrequency corresponding to the predetermined eigenform change in terms of time.

High accuracy and reliability featured in Coriolis mass flowmeters in single-phase flow operation—i.e., during flow of a physically homogenous medium—cannot be readily maintained and achieved in multi-phase flow, particular measures have to be taken here in order to simply acknowledge multi-phase flow; the present invention deals with the detection of multi-phase flow in Coriolis mass flowmeters.

A multi-phase flow is, in general, a flow that is made up of at least two phases with different physical characteristics. The phases, here, can be either of the same or of different materials. Homogenous and spatially limited sections are denoted as phases. The following are examples of such liquid-solid flow, gas-liquid flow, gas-solid flow, water-vapor flow or water-air flow.

It is known that in applications with multi-phase flow, substantial measurement inaccuracies occur, so that it is of great interest that the presence of multi-phase flow can be reliably detected.

SUMMARY OF THE INVENTION

The object of the present invention is thus, to provide a method for operating a Coriolis mass flowmeter and a corresponding Coriolis mass flowmeter that allows for reliable and potentially simple detection of multi-phase flow.

The method according to the invention for operating a Coriolis mass flowmeter in which the above object is met, is initially characterized in that the control and evaluation unit detects at least one first measured value for at least one state variable dependent on the amplitude in a multi-phase medium, that the measuring tube is excited by the oscillation generator to an oscillation with the excitation frequency and a second amplitude differing from the first amplitude, that the resulting oscillation of the measuring tube is detected and the control and evaluation unit determines at least a second measured value for the state variable dependent on the amplitude in a multi-phase medium from the determined resulting oscillation, and that the deviation of at least one of the first measured value from at least one of the corresponding second value is used as an indicator for the presence of a multi-phase flow.

The idea underlying the invention is to use such state variables, which are dependent on the amplitude in a multi-phase medium, of the Coriolis mass flowmeter to determine a multi-phase flow, so that different measured values for the state variables are obtained and a multi-phase flow can be determined by exciting the measuring tube to different oscillations with the same frequency but different amplitudes—only when the medium is multi-phase. This requires, of course, that the state variable does not have such an amplitude dependence when the medium is single-phase, or at least, has an amplitude dependence that is different in a distinguishable measure than in the case of a medium that is multi-phase.

The very significant advantage of the method is that practically no constructional changes—for example, in the form of additional sensors—have to be made on known resonance measuring systems, e.g., in the form of Coriolis mass flowmeters or density measuring unites in order to carry out this method, only a change in the control of known resonance measuring systems and the implementation of the evaluation method in the control and evaluation unit has to occur, which, however, in comparison, is easily possible, since only one suitable detection and evaluation of the measured value has to be performed.

The excitation of the measuring tube of a Coriolis mass flowmeter to an oscillation is a functional requirement in Coriolis mass flowmeters and the control of the oscillation at a certain amplitude is known per se and is already integrated in common Coriolis mass flowmeters for different reasons. The method according to the invention thus allows for a multi-phase flow to be detected with an exceptionally small additional effort, through which the user of a Coriolis mass flowmeter can reliably decide whether a mass flow or density value changed because the mass flow or the density of a homogeneous medium actually changed or if changed measured values are based on the presence of a multi-phase flow. The method is completely independent of the Coriolis mass flowmeter having straight or curved measuring tubes, having one, two or more than two measuring tubes, etc. There are also internal parameters in a Coriolis mass flowmeter, which are dependent on the amplitude, for example, the coupling factor between different excited oscillation modes should be mentioned here. The path and acceleration couplings acting in the same phase—often summarized into one coupling factor $k_{sb}$—are particularly suitable here in conjunction with the present invention, wherein in particular the different accelerations of measuring tube halves are caused by an asymmetrical distribution of the oscillating masses.

An advantageous design of the method is characterized in that the measuring tube is excited by the oscillation generator to an oscillation with the excitation frequency and at least one further amplitude different than the first amplitude and the second amplitude, that the resulting oscillation of the measuring tube is detected and the control and evaluation unit determines at least one additional measured value for the state variable (x) dependent on the amplitude for a multi-phase medium from the detected, resulting oscillation and that deviations in the measured values of at least one of the first measured value and/or at least one of the second measured value is used by at least one of the corresponding further measured values as an indicator for the presence of a further multi-phase flow or, respectively, medium phase. Thus, not only that a multi-phase flow exists or multiple medium phases exist can be differentiated, but, using the described procedure, it can also be differentiated how many phases are present in the flow or in the medium. This knowledge is used in a continuation of the method in that the measuring tube is excited by the oscillation generator to oscillations with the excitation frequency and, in this manner, many different amplitudes are excited until further multi-phase flows or medium phases can be differentiated, through which, then, consequently the number of multi-phase flows or medium phases is determined.

According to a preferred design of the method according to the invention, it is provided that the density of the medium, the mass flow of the medium through the measuring tube, or the eigenfrequency of the measuring tube is used for a certain eigenform as a state variable dependent on the amplitude in a multi-phase medium. Each of these three state variables shows a dependency on the amplitude of the oscillation at multi-phase flow and practically no dependency on the amplitude of the oscillation of the measuring tube at single-phase flow. Each of these variables can be used alone for detecting a multi-phase flow, of course, also two or all three of these variables can be determined and evaluated for detecting a multi-phase flow. In the mathematic description of Coriolis mass flowmeters, the density of the medium and the mass flow of the medium through the measuring tube appear more likely as parameters and not as state variables of the system in terms of system theory, however, they influence the state of the resonance measuring system; this in the sense in which "state variable" is to be understood.

By stating that a variable is dependent on the amplitude at multi-phase flow of the medium, then this does not indicate only a direct dependency of this state variable on the maximum deflection of the measuring tube, but any dependency that is caused by the change of amplitude of the measuring tube oscillation. When the amplitude of an oscillation is changed at a consistent oscillation frequency, then, of course, not only the deflection of the oscillation itself is changed, but also the velocity of the oscillation (first derivative of the deflection) and the acceleration achieved by the oscillation (second derivative of the deflection). The velocity and acceleration of the oscillating measuring tube are directly related to physical phenomena that occur at multi-phase flow and lead to detectability of multi-phase flow in the sense of the present invention. The flow characteristics are influenced in multi-phase flow in that the individual flow phases move relative to one another due to the density differences and that the imposing of the radial velocity required for density and flow measurement no longer occurs in a defined manner. This leads to discrepancies in the measurement of density as well as in flow measurement. These effects bring about that Coriolis mass flowmeters show density values of over 1000 kg/m3 when there are air bubbles in the flow (e.g., water).

In a further advantageous design of the method according to the invention, it is provided that the determined deviation, i.e., the deviation of the first measured value—measured at oscillation of the measuring tube with the first amplitude—from the second measured value—measured at the oscillation of the measuring tube with the second amplitude—is compared to a predetermined threshold value and the presence of a multi-phase flow is indicated when the threshold value is exceeded, regardless of how the indication of the multi-phase flow occurs (output of a signal observable by the user and/or only an internal electric signal (setting a flag) and/or transmitting a suitable field bus message to a connected process control system).

Preferably, the presence of a multi-phase flow is first indicated when the evaluation from two different amplitude-dependent state variables suggests a multi-phase flow, when, for example, the evaluation of two of the above-mentioned state variables density, mass flow and eigenfrequency change at the same time in a manner that suggests multi-phase flow. In this manner, the reliability of the determination of multi-phase flow is increased, since an actual change of the mass flow or the density that coincides by chance with a change in amplitude cannot be detected as a multi-phase flow by mistake. The presence of a multi-phase flow is thus first indicated when at least two determined deviations from two different amplitude-dependent state variables simultaneously exceed a predetermined threshold value.

Additionally or alternatively to this, the method according to the invention is advantageously carried out in such a manner that the measuring tube is excited by the oscillation generator successively to multiple oscillations with different amplitudes having the same excitation frequency and the presence of a multi-phase flow is first indicated at a number of measured value deviations following one another of at least one previous measured value from at least one corresponding subsequent measured value. It should be taken into consideration here that the amplitudes of oscillations following one another have to be different from one another; it is thus not necessary that all of the amplitudes are overall different from one another. For example, there could be two different amplitude values that change alternately. In this variation of the method, a multi-phase flow can also be detected with great certainty, since it is ruled out that only a sudden actual change of one of these state variables is detected, since the likelihood is negligible that only one of the state variables changes exactly in the temporal pattern with which the amplitudes of the measuring tube oscillation are also changed according to the method.

Preferably, the lowest resonance frequency of the measuring tube is chosen as excitation frequency. By operating the measuring tube in resonance, the desired oscillation can be achieved with the least possible energy effort, so that the power loss is low overall. The required power is then at the lowest all in all when the lowest resonance frequency is used for the oscillation of the measuring tube. When the resonance frequency of the measuring tube is discussed here, then the oscillation-capable complete system is meant, of course, whose main component is the measuring tube.

It has been shown to be overall of advantage when the method according to the invention is carried out in such a manner that time for which the second, subsequent amplitude is maintained after it has been switched from a first, previous amplitude to the second, subsequent amplitude, is at least so long that the adjustment process within the Coriolis mass flowmeter caused by the amplitude switch has ceased. Transient characteristics can have different causes here and can appear at different positions. Transient events can be caused by the amplitude control; however, they can also be caused by transient events in certain used electronic components. For this reason, it can be advantageous to maintain a predetermined amplitude of the measuring tube oscillation at least for a few seconds and to take a measurement first towards the end of this time frame or, respectively, to use only those signal samples that were detected in the oscillated state of the system.

The method according to the invention is also advantageous because it can be easily carried out parallel to the actual flow measurement, since the method for detection of a multi-phase flow does not require a detection mode differing from the normal flow measuring mode, rather only a change of amplitude has to be implemented of the measuring tube oscillation stringently required for flow measurement.

In a further design, the method for the detection of a multi-phase flow is not always carried out simultaneously with the actual flow measurement, but is switched on in greater time intervals of the flow measurement, so that a regular diagnosis is guaranteed.

The invention further relates to a resonance measuring system, in particular a Coriolis mass flowmeter equipped with the above-mentioned technical details of the device, in which the control and evaluation unit is specifically designed in such a manner that the Coriolis mass flowmeter can carry out the method according to the invention described above for detecting a multi-phase flow during operation; the control and evaluation unit is then programmed in such a manner that the Coriolis mass flowmeter can carry out the detection method and the control and evaluation unit does not have to be re-programmed in order to do so.

In detail there are many possibilities for designing and further developing the method according to the invention for operation a Coriolis mass flowmeter and the Coriolis mass flowmeter according to the invention as will be apparent from the following description of preferred embodiments in conjunction with the accompanying drawings.

DETAILED DESCRIPTION OF THE INVENTION

Figure 1:
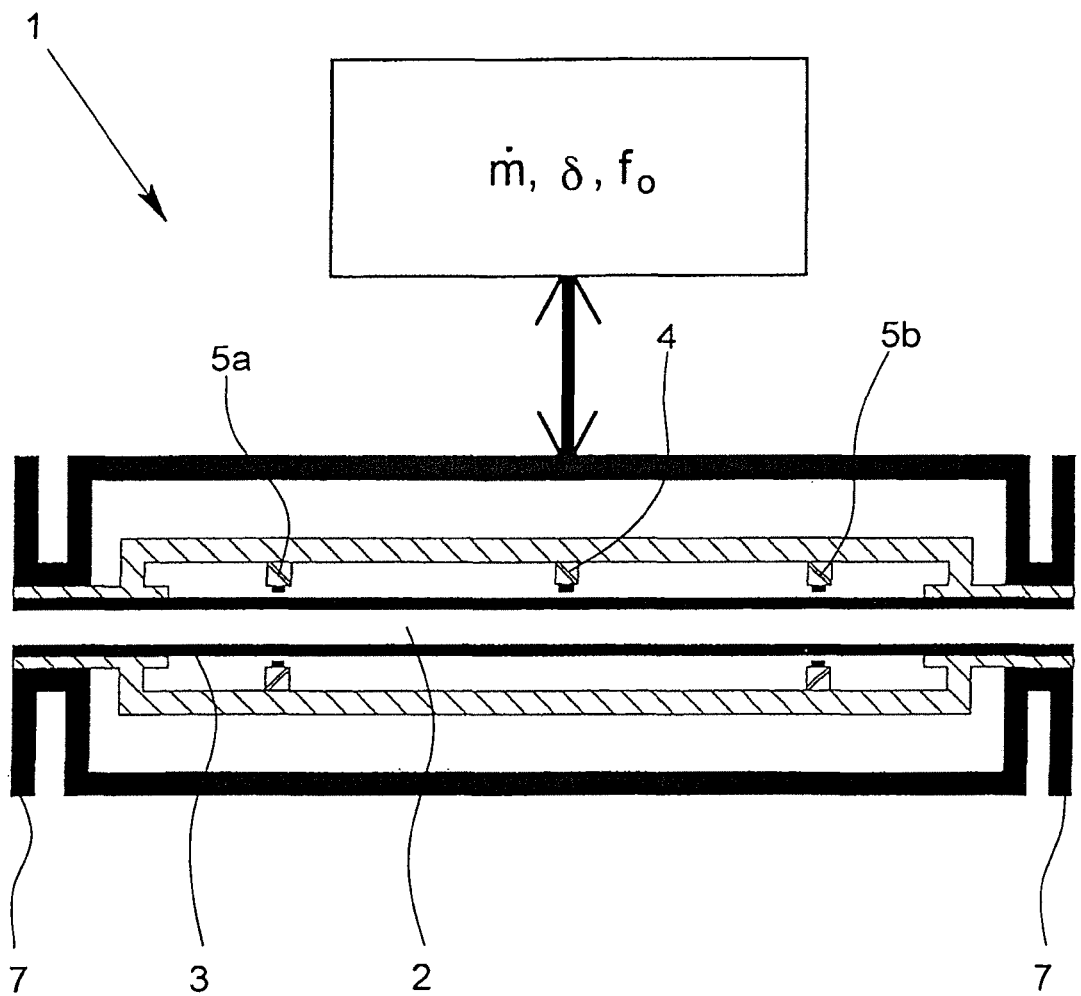
FIG. 1 is aschematic representation of a Coriolis mass flowmeter that is known per se that is provided with a connected control and evaluation unit according to the present invention.

A resonance measuring system in the form of a Coriolis mass flowmeter, known constructively per se, is shown very schematically in FIG. 1 as having a measuring tube 3 with medium 2 flowing through it, an oscillation generator 4 and oscillation sensors 5a, 5b as well as a control and evaluation unit 6. The oscillation sensors 5a, 5b, of course, need not be provided on both sides of the measuring tube.

The measuring tube 3 can be excited by the oscillation generator 4 into oscillation with a predetermined excitation frequency and first amplitude, which is necessary for the functionality of an elementary implementation of the flow measurement in Coriolis mass flowmeters. The oscillation of the measuring tube 3 resulting from the excitation is detected by the oscillation sensors 5a, 5b, wherein the mass flow through the measuring tube 3 can be determined from the phase difference of the oscillations at the left and right sides of the measuring tube 3.

The control and evaluation unit 6 is connected with the mechanical parts of the Coriolis mass flowmeter 1 in such a manner that the control and evaluation unit 6 generates signals that control the oscillation generator 4 and the measuring signals detected by the oscillation sensors 5a, 5b can be transmitted to the control and evaluation unit 6. It is not important for the further representation how the control and evaluation unit 6 is implemented in detail, it could consist of one single electric component or it could consist of a distributed system of multiple components, none of this is of importance.

The Coriolis mass flowmeter can be connected via a flange 7 to a process and an external piping network. Different state variables x of the total system can be determined from the oscillation signals detected by the oscillation sensors 5a, 5b—provided that there is a suitable control of the measuring tube 3—in addition to the original variable of the mass flow $\dot{m}$, for example, also the density $\rho$ of the medium found in the measuring tube and the eigenfrequency $f_0$ of the oscillation-capable system. How these variables are determined from the oscillation signals is adequately known from the prior art.

The control and evaluation unit 6 is designed in such a manner that it determines a first measured value or derived value $x_i$ for at least one state variable x dependent on the amplitude in a multi-phase medium out of the detected, resulting oscillation—oscillation with the first amplitude. The measuring tube 3 is then excited to an oscillation by the oscillation generator 4 with the same excitation frequency, but a second amplitude differing from the first amplitude, and in turn, the resulting oscillation of the measuring tube 3 is detected, whereupon the control and evaluation unit 6 determines at least a second measured value or derived value $x_j$ for the state variable x dependent on the amplitude in a multi-phase medium from the resulting oscillation.

Due to the amplitude dependency of the state variable x, a deviation between the first measured value $x_i$ and the second measured value $x_j$ at a multi-phase flow results so that the deviation of the measured values is used as an indicator for the presence of a multi-phase flow.

As can be seen in FIG. 1, this method can be carried out using any common Coriolis mass flowmeter, and so long as the described, method-related control and evaluation is provided by the control and evaluation unit 6 no constructional modification of the Coriolis mass flowmeter 1 is necessary.

The density ρ of the medium 2 and the mass flow ṁ of the medium 2 through the measuring tube 3 are used as amplitude-dependent state variables in the Coriolis mass flowmeter 1 shown in FIG. 1. In other embodiments, not only are the above-mentioned external variables used, but alternately or additionally, also internal variables of the Coriolis mass flowmeter such as, for example, the time difference of both measuring tube halves, the oscillation frequency and the asymmetry of the mass filling of the measuring tube halves.

Figure 2:
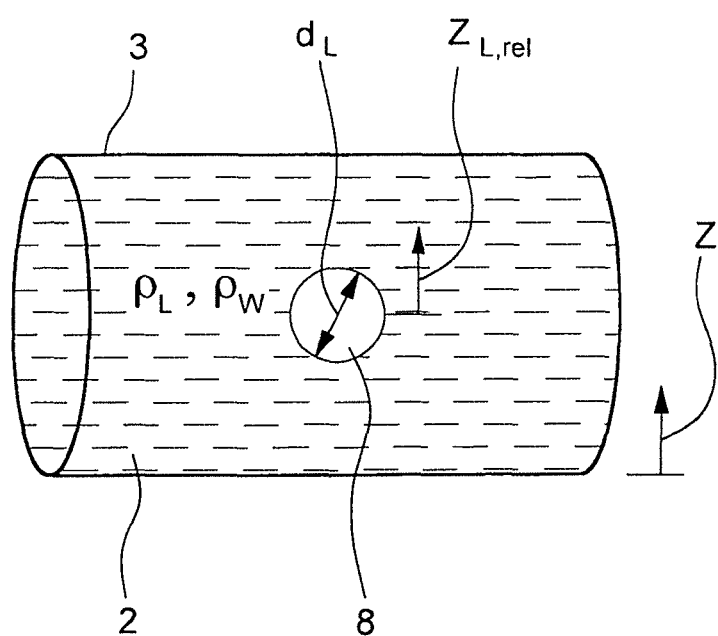
FIG. 2 is a schematic representation of air bubble in a measuring tube section filled with water.

As has already been described in the introduction, the fundamental causes for the occurrence of measuring inaccuracies at multi-phase flow are secondary flows in the measuring tube 3 that are caused by different densities of the multi-phase flows. This interrelation is to be described in FIG. 2. A spherical air bubble 8 in the middle of a measuring tube 3 filled with water is shown in FIG. 2. The air bubble 8 has the diameter $d_L$ and has a density $\rho_L$ at the given temperature and pressure conditions; the water has a corresponding density of $\rho_W$. When the measuring tube 3 is accelerated to transversal oscillation in its first eigenform by an oscillation generator (not shown), different forces act on the air bubble 8. If, for the sake of simplification, the gravity and the compressibility of the air bubble are not taken into consideration here, the balance of forces for the air bubble is as follows:

$$\underbrace{\rho_L V_L \ddot{z}_{L,rel}}_{1} + \underbrace{\frac{1}{2} C_D \rho_W A_L \dot{z}_{L,rel}^2}_{2} + \underbrace{C_\alpha \rho_W V_L \ddot{z}_{L,rel}}_{3} = \underbrace{(\rho_W - \rho_L) V_L \ddot{z}_{L,rel}}_{4}$$

In the above equation,
$\ddot{z}_{L,rel}$ is the relative acceleration of the air bubble
$\dot{z}_{L,rel}$ is the relative velocity of the air bubble
$\rho_L, \rho_W$ is the density of the air bubble, density of water
$V_L$ is the volume of the air bubble
$d_L$ is the diameter of the air bubble
$A_L$ is the cross section of the air bubble
$C_D$ is the resistance coefficient
$C_\alpha$ is the "virtual mass" coefficient It is expressed in the given equation that the external forces (right side of the equation expression 4) transmitted to the air bubble 8 are in balance with the internal reaction forces acting on the air bubble 8, namely the inertial force of the air bubble mass (expression 1), the resistance force due the movement of the air bubble within the medium 2 (expression 2) and the inertial force of the so-called "virtual mass" (expression 3). The virtual mass takes into consideration that the medium mass displaced by the air bubble also has to be accelerated. It should be taken into account here that the forces formulated are based on the relative movement of the air bubble in water ($Z_{L,rel}$).

It can be derived from the equation that the air bubble 8 implements a relative movement in respect to the water 2, which can be clearly described when the acceleration conferred due to the excitation of the measuring tube 3 is understood as gravitational acceleration. The inertial acceleration of the air bubble in this case consequently corresponds to the gravitational acceleration. Exactly as the air bubble in the gravitational field of the earth moves upward against gravity, the air bubble travels against the inertial acceleration in the case of the accelerated measuring tube. The cause of this behavior is the difference in density between the air bubble 8 and the surrounding medium 2. Since the air bubble 8 runs ahead of the medium in the oscillation, it displaces the water in front of it, which flows back in an opposite movement with the relative velocity $\dot{z}_{L,rel}$ of the air bubble 8. As a result, it is determined, at any rate that, at a multi-phase flow, a directed, radial relative movement in the flow occurs due to forced movement of the measuring tube, which is dependent on the amplitude of the forced deflection (namely from the velocity and acceleration of the measuring tube movement resulting from this) and which leads to the measured values dependent on the amplitude to be detected and detected by the method according to the invention.

Figure 3:
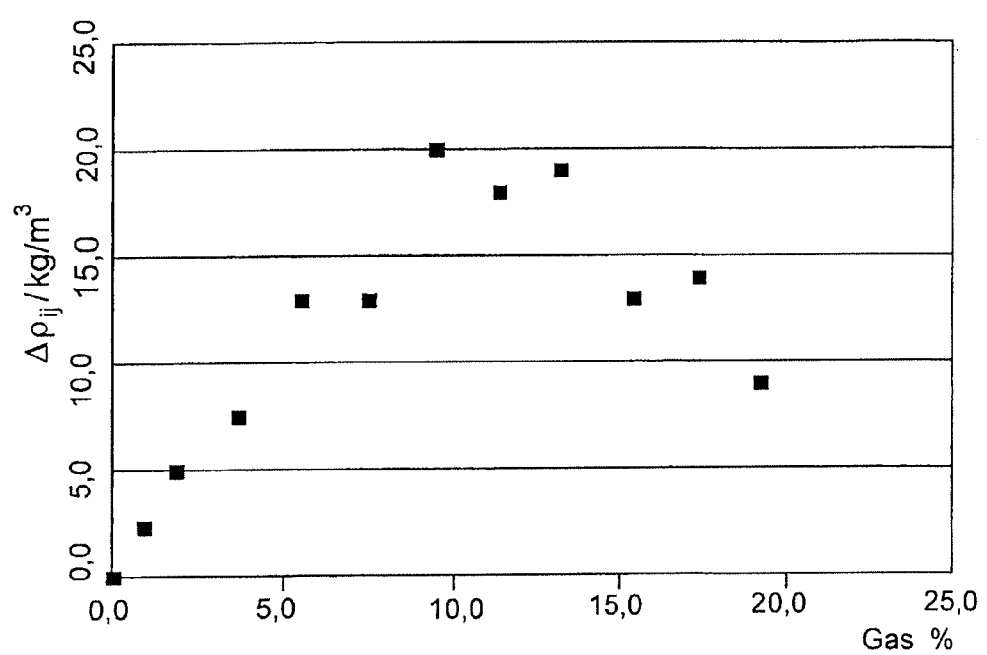
FIG. 3 is a graph showing deviations of measured values which were detected at different oscillation amplitudes at differently defined multi-phase flows.

In FIG. 3, measured results are shown, namely the deviations $\Delta\rho_{ij}$ of density measured values $\rho_i$ and $\rho_j$ over the air proportion (gas %) in a water flow, wherein the amplitudes of the first oscillation and the second oscillation of the measuring tube 3 differ by about 33%. It can be clearly seen that in a single-phase flow (gas percent 0%), there is no presence of a measurement difference at different amplitudes, however, the measurement difference clearly occurs in a multi-phase flow and, thus, is a suitable indicator for detecting a multi-phase flow.

What is claimed is:

1. Method for operating a resonance measuring system having at least one measuring tube with a medium flowing through it, at least one oscillation generator, at least one oscillation sensor, and at least one control and evaluation unit, comprising the steps of:
    exciting the measuring tube by the oscillation generator to oscillation with a predetermined excitation frequency and a first amplitude,
    detecting the resulting oscillation of the measuring tube with at least one oscillation sensor,
    using the control and evaluation unit to determine at least one first measured value ($x_i$) for at least one state variable (x) that is dependent on the amplitude in a multi-phase medium,
    exciting the measuring tube by the oscillation generator to oscillation with the excitation frequency and a second amplitude which differs from the first amplitude,
    detecting the resulting oscillation of the measuring tube with the second amplitude and using the control and evaluation unit to determine at least a second measured value ($x_j$) for the at least one state variable (x) that is dependent on the amplitude in a multi-phase medium from the determined resulting oscillation, and
    using a deviation ($\Delta x_{ij}$) of at least one of the first measured value ($x_i$) from at least one of the corresponding second values ($x_j$) as an indicator for the presence of a multi-phase flow.

2. Method according to claim 1, wherein the measuring tube is excited by the oscillation generator to an oscillation with the excitation frequency and at least one further amplitude differing from the first amplitude and the second amplitude, wherein the resulting oscillation of the measuring tube is detected and the control and evaluation unit determines at least one additional measured value for the state variable (x) dependent on the amplitude for a multi-phase medium from the detected, resulting oscillation and wherein deviations in the measured values of at least one of at least one first measured value and at least one second measured value is used by at least one of the corresponding further measured values ($x_j$) as an indicator for the presence of a further multi-phase flow or medium phase.

3. Method according to claim 1, wherein the measuring tube is excited by the oscillation generator to oscillations with the excitation frequency and many different amplitudes are excited until further multi-phase flows or medium phases can no longer be differentiated, the number of multi-phase flows or medium phases being determined therefrom.

4. Method according to claim 1, wherein the density (ρ) of the medium (2) and/or the mass flow ṁ of the medium (2) through the measuring tube (3) and/or the eigenfrequency $f_0$, of the measuring tube (3) is/are used as a state variable (x) for a certain eigenform dependent on the amplitude in a multi-phase medium (2).

5. Method according to claim 1, wherein the determined measured value deviation ($\Delta x_{ij}$) is compared to a predetermined threshold value and the presence of a multi-phase flow is indicated when the threshold value is exceeded.

6. Method according to claim 1, wherein the presence of a multi-phase flow is first indicated when at least two determined measured value deviations ($\Delta x_{ij}$) from two different state variables (x) dependent on amplitude exceed a predetemiined threshold value at the same time.

7. Method according to claim 1, wherein the at least one measuring tube is excited by the oscillation generator successively to a number of oscillations with the first frequency, wherein the amplitudes of oscillations following one another differ from one another and the presence of a multi-phase flow is first indicated at a number of measured value deviations following one another of at least one previous measured value from at least one corresponding subsequent measured value.

8. Method according to claim 1, wherein the lowest resonance frequency ($f_0$) of the measuring tube is chosen as the excitation frequency.

9. Method according to claim 1, wherein a time for which the second, subsequent amplitude is maintained after it has been switched from a first, previous amplitude to the second, subsequent amplitude, is at least so long that an adjustment process within the resonance measuring system caused by the amplitude switch has ceased.

10. Method according to claim 1, wherein detecting of multi-phase flow is carried out at the same time as at least one of an actual flow measurement and an actual density measurement.

11. Resonance measuring system, comprising:
   at least one measuring tube with a medium flowing through it,
   at least one oscillation generator,
   at least one oscillation sensor, and
   at least one control and evaluation unit,
   wherein the oscillation generator is adapted for exciting the measuring tube to oscillation with a predetermined excitation frequency and a first amplitude, and for exciting the measuring tube to oscillation with said predetermined excitation frequency and a second amplitude which differs from the first amplitude,
   wherein the at least one oscillation sensor is adapted for detecting oscillation of the measuring tube,
   wherein the control and evaluation unit adapted for determining at least one first measured value ($x_i$) for at least one state variable (x) that is dependent on the amplitude in a multi-phase medium, for determining at least a second measured value ($x_j$) for the at least one state variable (x) that is dependent on the amplitude in a multi-phase medium from the determined detected oscillations, and for using a deviation ($\Delta x_{ij}$) of at least one of the first measured value ($x_i$) from at least one of the corresponding second values ($x_j$) as an indicator for the presence of a multi-phase flow.

12. Resonance measuring system according to claim 11, wherein resonance measuring system is in the form of one of a Coriolis mass flowmeter and a density measuring unit.

* * * * *